US 6,542,770 B2

(12) United States Patent
Zylka et al.

(10) Patent No.: US 6,542,770 B2
(45) Date of Patent: Apr. 1, 2003

(54) METHOD OF DETERMINING THE POSITION OF A MEDICAL INSTRUMENT

(75) Inventors: Waldemar Zylka, Hamburg (DE); Jörg Sabczynski, Norderstedt (DE); Jürgen Weese, Henstedt-Ulzburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 112 days.

(21) Appl. No.: 09/773,421

(22) Filed: Feb. 1, 2001

(65) Prior Publication Data

US 2001/0027263 A1 Oct. 4, 2001

(30) Foreign Application Priority Data

Feb. 3, 2000 (DE) .......................................... 100 04 764

(51) Int. Cl.[7] ................................................. A61B 5/05
(52) U.S. Cl. ..................................................... 600/424
(58) Field of Search ................................. 600/424, 425, 600/426, 427, 428, 429, 401; 378/4, 21, 23, 41, 900, 163, 164, 20

(56) References Cited

U.S. PATENT DOCUMENTS 4,907,252 A * 3/1990 Aichinger et al. .......... 324/309
5,251,635 A * 10/1993 Dumoulin et al. .......... 128/899
6,236,704 B1 * 5/2001 Navab et al. .................. 378/19
6,243,439 B1 * 6/2001 Arai et al. ................... 378/162
6,377,837 B1 * 4/2002 Coutts et al. ............... 600/423

FOREIGN PATENT DOCUMENTS

EP 0857461 A2 8/1998 ............ A61B/6/00
EP 0880109 A2 11/1998 ............ G06T/11/00

* cited by examiner

Primary Examiner—Teresa Walberg
Assistant Examiner—Daniel Robinson
(74) Attorney, Agent, or Firm—John Vodopia

(57) ABSTRACT

Method and device for determining the position of a medical instrument, partially introduced into an object being examined, in a three-dimensional image data set of the object. In order to achieve a high accuracy of the position determination and minimize the expenditure required and thus save intricate registration steps prior to an intervention, simultaneously with the acquisition of an X-ray image, the spatial positions of the X-ray image and the spatial position of a medical instrument are acquired. Then, the spatial correlation between an X-ray image and a three-dimensional image data set is determined. This correlation is used to transform the spatial position of the medical instrument into a position relative to the three-dimensional image data set. This enables the formation of images containing image information acquired pre-operatively as well as intra-operatively, and also the reproduction of the instantaneous position of the medical instrument in the images.

20 Claims, 2 Drawing Sheets

METHOD OF DETERMINING THE POSITION OF A MEDICAL INSTRUMENT

BACKGROUND OF THE INVENTION

1. Field of the Invention

The invention relates generally to a method for determining the position of a medical instrument partially introduced into an object to be examined, in a three-dimensional image data set of the object to be examined, and also relates to a device for carrying out such a method.

2. Description of Related Art

A method and device for determining the position of a medical instrument in a two-dimensional image data set are known from EP 857 461 A2. Therein, X-ray images of the examination zone of an object to be examined, for example a patient, are acquired intra-operatively by means of a C-arm X-ray device, while the position of the object to be examined, or the patient table, and the medical instrument relative to the X-ray device is measured at the same time by means of an optical position measuring device. The position of the medical instrument can subsequently be transformed into a position relative to one or more of the acquired X-ray images, so that the respective instantaneous position can always be reproduced in one or more X-ray images. A method of this kind can serve as a navigational tool for the physician during the treatment of a patient. However, it has the drawback that no intra-operative three-dimensional image information is available for the navigation. However, an intervention can be planned on the basis of a pre-operative three-dimensional data set, but only two-dimensional X-ray images can be acquired intra-operatively and the position of the medical instrument can be determined and indicated only in such intra-operatively acquired two-dimensional X-ray images.

Furthermore, methods are known in which the position of a medical instrument is intra-operatively determined so as to be transformed into a position relative to a pre-operatively acquired three-dimensional image data set. However, during the acquisition of the three-dimensional image data set the patient must be provided pre-operatively with special markers which are also reproduced in the three-dimensional image data set and are approached by a special pointer directly before the operation so as to determine their positions in space. An intra-operatively measured spatial position of a medical instrument can then be transformed into a position relative to the three-dimensional image data set by utilizing the positions of such markers which are thus known in spatial co-ordinates and in 3D image coordinates. Such methods, however, have the drawback that no instantaneous image information concerning the anatomy of the patient is used whereas during the intervention the anatomy regularly changes relative to the state of the anatomy during the pre-operative acquisition of the 3D image data set.

OBJECTS AND SUMMARY OF THE INVENTION

Therefore, it is an object of the present invention to provide a method for determining the position of a medical instrument, partially introduced into an object to be examined, in a three-dimensional image data set of the object to be examined that avoids the above-mentioned drawbacks and enables a high accuracy to be achieved at an expenditure which is as small as possible. Moreover, it is also an object of the present invention to provide a device which is suitable for carrying out such a method.

These objects are achieved by means of a method including the steps of acquiring a three-dimensional image data set of the object, acquiring a two-dimensional X-ray image of the object, determining spatial positions of the X-ray image and the medical instrument, determining a spatial correlation between the acquired X-ray image and the acquired three-dimensional image data set, and determining the position of the medical instrument in the three-dimensional image data set from the determined spatial position of the medical instrument based on the determined spatial correlation between the acquired X-ray image and the acquired three-dimensional image data set. These objects are also achieved by means of a device comprising an X-ray device for acquiring a two-dimensional X-ray image of the object, a position measuring device for measuring the spatial positions of the X-ray image and the medical instrument when introduced into the object, and a processor for determining the spatial correlation between the X-ray image and the three-dimensional image data set. The processor determines the position of the medical instrument in the three-dimensional image data set from the spatial position of the medical instrument by means of the spatial correlation between the X-ray image and the three-dimensional image data set.

The present invention is based on the recognition of the fact that an intra-operative two-dimensional X-ray image can be advantageously used to transform the intra-operatively measured position of the medical instrument into a position relative to a three-dimensional image data set which will usually have been pre-operatively acquired. According to the invention, to this end, not only the position of the medical instrument but the position in space of the X-ray image is measured intra-operatively. Using a suitable registration method, the spatial correlation between this X-ray image and the three-dimensional image data set is subsequently determined, thus yielding something resembling the spatial position of the three-dimensional image data set. This knowledge enables a simple determination of the position of the medical instrument relative to the three-dimensional image data set because the spatial position of the medical instrument has been acquired directly before that. The present invention thus enables a simple determination of the position of a medical instrument in a three-dimensional image data set without it being necessary to provide the patient during the acquisition of the image data set with special markers that are to be reproduced and must be registered again immediately before the operation. Moreover, intra-operatively acquired image data providing exact information concerning the anatomy of the patient are processed, so that the accuracy of the determination of the position is enhanced.

Another embodiment of the present invention includes means for determining the spatial position of the X-ray image; such means can also be used to determine the spatial position of the medical instrument. The position measuring device used for this purpose may be of a variety of constructions; for example, it may include optical cameras, infrared cameras and/or electromagnetic detectors that are capable of determining the three-dimensional position of corresponding markers, for example, optical light-emitting diodes, infrared diodes or electromagnetic transmitters.

Additional embodiments provide for further possibilities for determining the spatial correlation between the X-ray image and the three-dimensional image data set. To this end, the overall three-dimensional image data set, or one or more sub-volumes or individual objects or structures that are particularly prominent in the image data set or individual voxels of the image data set are compared with the X-ray image or searched in the X-ray image. This operation is preferably performed iteratively. Such an advantageous method of comparison is known from EP 880 109 A2 to which reference is made explicitly herein and whose disclosure is considered to be included in the present application. Pseudo-projection images are thus formed from the three-dimensional image data set and compared with the X-ray image, the parameters underlying the formation of the pseudo-projection image, for example the imaging scale, projection direction etc., being iteratively varied until the pseudo-projection image and the X-ray image match as well as possible. The spatial correlation between the X-ray image and the 3D image data set is thus found. can be executed intra-operatively and continuously, and hence it can serve as a navigational tool for the physician during the treatment of a patient and can continuously deliver instantaneous information concerning the anatomy and the position of the medical instrument.

The three-dimensional image data set may be used to derive an image in which the position of the medical instrument or the instrument itself is reproduced. This also serves as to aid the attending physician during an operation. Different images can then be formed, for example, layer images or projection images that were formed from the three-dimensional image data set and cannot be formed by means of the intra-operatively used X-ray device, for example, combination images from pre-operatively acquired and intra-operatively acquired image data, vascular systems or pre-operatively determined navigation plans.

The three-dimensional image data set may be acquired pre-operatively by means of an arbitrary imaging device and an X-ray fluoroscopy device, for example a C-arm X-ray device, is used intra-operatively. As a result, images from different imaging modalities and with a different information contents can thus also be intra-operatively presented to the physician during the treatment.

A device according to the invention which is suitable for carrying out the described method particularly advantageously includes an X-ray device, a position measuring device and an arithmetic unit or processing unit.

BRIEF DESCRIPTION OF THE DRAWINGS

The invention will be described in detail hereinafter with reference to the drawings, wherein.

DETAILED DESCRIPTION OF THE INVENTION

Figure 1:
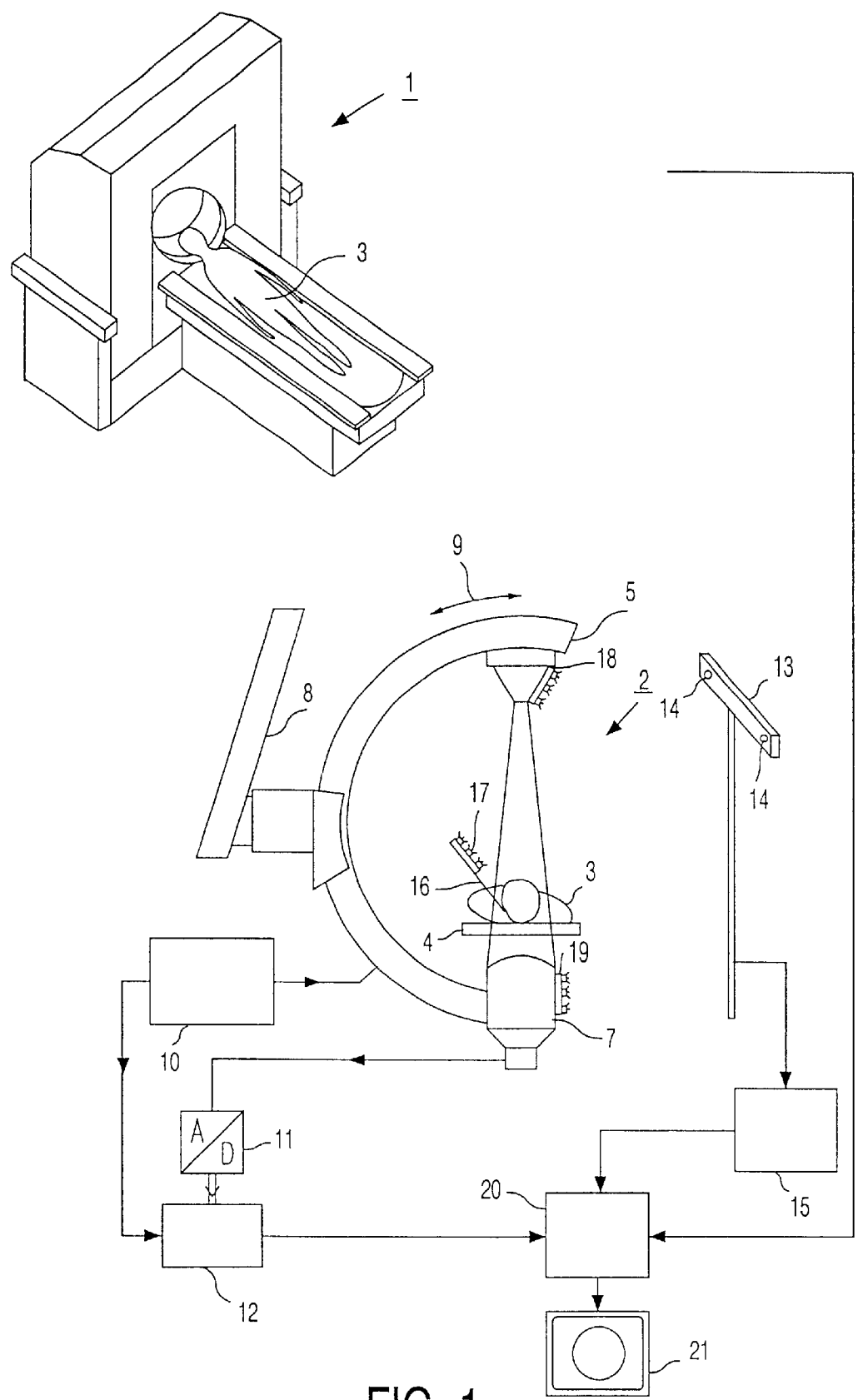
FIG. 1 shows diagrammatically a device according to the invention.

FIG. 1 shows a computed tomography apparatus 1 which is employed to form a series of computer tomograms of a patient 3 prior to a surgical intervention. The tomograms represent parallel slices which extend perpendicularly to the longitudinal axis of the patient. Such computer tomograms form a three-dimensional image data set for a three-dimensional reproduction of the examination zone of the patient 3. The surgical intervention to be performed at a later stage, for example, can be accurately planned on the basis of such an image data set.

During the invention two-dimensional X-ray images of the patient 3 on a surgical table 4 are continuously acquired by means of an X-ray device 2. To this end, a C-arm X-ray device is used in the present case; this device includes an X-ray source 6 and an X-ray detector 7 which are mounted on a C-arm which is supported by a stand 8 (not shown). The C-arm is pivotable about a horizontal axis at least in the direction of an arrow 9. The X-ray image detection device 7 outputs its output signals, via an analog-to-digital converter 11, to an image memory 12 which is connected to an arithmetic unit 20 (a processing unit). The X-ray device 2 is controlled by means of a control unit 10.

Also provided is a position measuring device 13 with two infrared CCD cameras 14 which are arranged on a stand to the side of the examination zone. The spatial positions of correspondingly constructed infrared light-emitting diodes can be determined by means of the cameras 14. In order to determine the position of a medical instrument 16 used during the intervention, in this case a biopsy needle, the end of the biopsy needle 16 which projects from the patient is provided with three infrared light-emitting diodes 17 in defined positions. In order to determine the position of the X-ray device 2, or the imaging geometry of the X-ray device 2, during the acquisition of X-ray images during the operation, three light-emitting diodes 18 and 19 are provided on each of the X-ray source 6 and the X-ray detector 7, respectively. The spatial position of an acquired X-ray image can be determined from the imaging geometry thus determined, that is, the position of the X-ray image relative to the patient 3. This calculation and the storage of the positions determined take place in a position calculation unit 15 whose results are applied to the arithmetic unit 20.

The arithmetic unit 20 receives not only the intra-operatively acquired X-ray images and the measured positions, but also the image data set pre-operatively acquired by the computed tomography apparatus 1. From such data, it determines the spatial correlation between the two-dimensional X-ray image and the three-dimensional image data set by means of a comparison method explained below. After determination of this correlation rule, the spatial position of the medical instrument 16 can be transformed into a position relative to the three-dimensional image data set and one or more images can be formed from the three-dimensional image data set and/or the intra-operatively acquired X-ray image, which images can be displayed on a monitor 21 and the position of the medical instrument can be reproduced therein.

Figure 2:
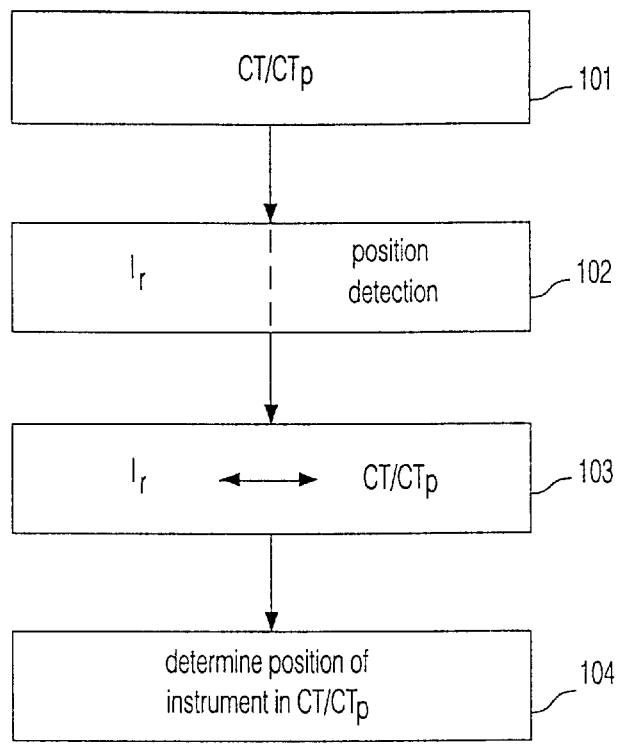
FIG. 2 shows a diagram illustrating the execution of the method according to the invention.

FIG. 2 again shows the individual steps of the method in the form of a flow chart. During the pre-operatively executed step 101 a three-dimensional image data set CT is acquired by means of the computed tomography apparatus; this image data set is a three-dimensional representation of the absorption distribution within a volume to be examined. From this volume there may also be selected a sub-volume $CT_p$ which region is a region of particular interest for the later intervention. This selection can be performed manually or also automatically by segmentation.

The intra-operatively executed subsequent steps 102 to 104 can be carried out continuously or repeatedly with desired time intervals or at given instants during an intervention. During the step 102 a two-dimensional X-ray image $I_r$ and the positions of the imaging geometry and the medical instrument are determined simultaneously. Subsequently, in the step 103, the correlation rule between the X-ray image $I_r$ and the overall volume CT, or the sub-volume $CT_p$, of the three-dimensional image data set is determined. Finally, in the step 104 this rule is used to determine the position of the medical instrument in the overall volume CT or the sub-volume $CT_p$ of the image data set and possibly to form suitable images.

Figure 3:
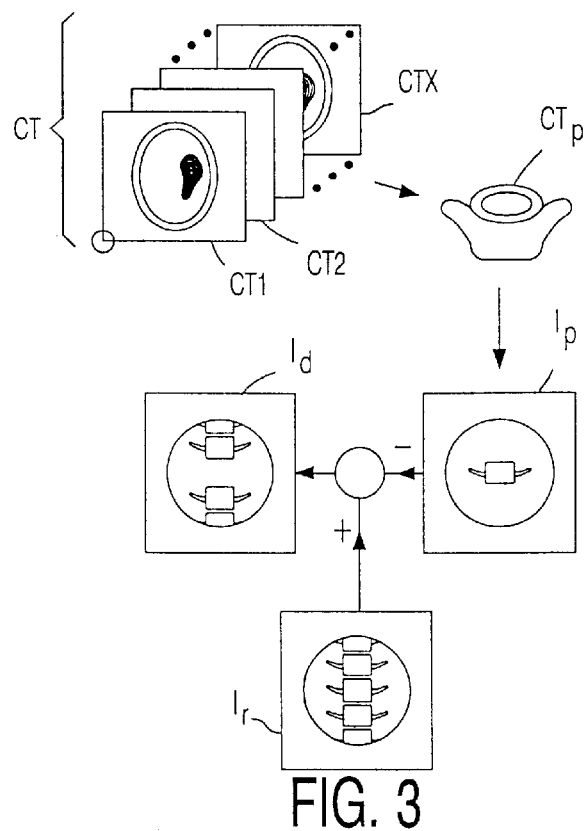
FIG. 3 shows a block diagram illustrating the method according to the invention.

The comparison method for determining the correlation rule will be described in detail hereinafter with reference to FIG. 3. The three-dimensional image data set CT is formed from a plurality of layer images CT1, CT2, . . . , CTX acquired by the computed tomography apparatus. From this set, there is selected a sub-volume $CT_p$ which is relevant to the later intervention and represents, for example, a vertebra in the case shown.

The spatial transformation or correlation between the image of the patient, in particular the image of the segmented vertebra, represented by the CT data set and the spatial position of this vertebra is determined by means of the intra-operatively acquired X-ray image $I_r$. To this end, pseudo-projection images $I_p$ are formed of the sub-volume $CT_p$. The magnitude of the pseudo-projection image $I_p$ should correspond to that of the X-ray image $I_r$. The position of the projection point from which the projection takes place from the sub-volume $CT_p$ to the pseudo-projection image $I_p$ corresponds to the position of the X-ray source (or the focal spot of the X-ray source emitting the X-rays) in relation to the X-ray detector during the X-ray exposure. Generally, the starting position of the sub-volume $CT_p$ initially selected in relation to the projection point and the projection direction do not correspond to the position and the orientation of the real sub-volume in relation to the X-ray source and the X-ray detector during the acquisition of the X-ray image. Therefore, these projection parameters of the sub-volume $CT_p$ are varied in relation to the projection point and the plane of the projection image $I_p$ until a difference image $I_d$, derived from the difference between the X-ray image $I_r$ and the pseudo-projection image $I_p$, produces an image of the vertebra $CT_p$ which is as good as possible. This is the case when the position and orientation of the vertebra $CT_p$ on which the pseudo-projection image $I_p$ is based correspond to the position and the orientation of the real vertebra in relation to the X-ray source and the X-ray detector. For a further explanation of this method, reference is again made to the cited EP 880 109 A2.

The described method enables a very accurate determination of the correlation between the X-ray image $I_r$ and the three-dimensional image data set CT in the two directions perpendicular to the direction of the X-ray beam. Such a determination, however, is substantially less accurate in the direction of the central beam. This situation, however, can be improved by forming a second X-ray image with a beam path extending perpendicularly to that used for the first X-ray image and by carrying out the comparison method also by means of this second X-ray image.

The invention is not limited to the embodiment shown which is given merely by way of example. The three-dimensional image data set can also be acquired by means of a different imaging system. Moreover, the intra-operatively used X-ray device and the position measuring device may also have a different construction for as long as the necessary functionality is provided. The exact configuration of the steps of the method, in particular the determination of the correlation rule between the three-dimensional image data set and the two-dimensional X-ray images, may also be completely different. The described comparison method is given merely as an example of the determination of such a correlation.

What is claimed is:

1. A method for determining the position of a medical instrument, partly introduced into an object being examined, in a three-dimensional image data set of the object, the method comprising the steps of:

acquiring a three-dimensional image data set of the object, then acquiring a two-dimensional X-ray image of the object, determining spatial positions of the X-ray image and the medical instrument, determining a spatial correlation between the acquired X-ray image and the acquired three-dimensional image data set, and determining the position of the medical instrument in the three-dimensional image data set from the determined spatial position of the medical instrument using the determined spatial correlation between the acquired X-ray image and the acquired three-dimensional image data set.

2. A method as claimed in claim 1, wherein the step of determining the spatial position of the X-ray image comprises the step of determining the spatial positions of at least one imaging element of an X-ray device.

3. A method as claimed in claim 1, wherein the step of determining the spatial correlation between the X-ray image and the three-dimensional image data set comprises the step of determining the spatial correlation using a comparison method.

4. A method as claimed in claim 3, wherein the step of determining the spatial correlation using a comparison method comprises the steps of comparing a sub-volume of the three-dimensional image data set with the X-ray image and iteratively determining a correlation rule.

5. A method as claimed in claim 3, wherein the step of determining the spatial correlation using a comparison method comprises the steps of determining a pseudo-projection image from at least a data sub-set of the three-dimensional image data set, comparing the pseudo-projection image with the X-ray image, and iteratively varying the parameters underlying the determination of the pseudo-projection image until optimum correspondence is achieved between the pseudo-projection image and the X-ray image.

6. A method as claimed in claim 1, wherein the steps of acquiring the two-dimensional X-ray image of the object, determining the spatial positions of the X-ray image and the medical instrument, determining the spatial correlation between the acquired X-ray image and the three-dimensional image data set, and determining the position of the medical instrument in the three-dimensional image data set are performed intra-operatively and continuously.

7. A method as claimed in claim 1, further comprising the steps of displaying an image formed from the three-dimensional image data set and reproducing the position of the medical instrument or the instrument itself in the displayed image.

8. A method as claimed in claim 1, wherein the X-ray image is acquired by means of an X-ray fluoroscopy device and the three-dimensional image data set is acquired in a pre-operative manner by means of a computed tomography apparatus, a magnetic resonance tomography apparatus, an ultrasound device or an X-ray device.

9. A method as claimed in claim 1, wherein the two-dimensional X-ray image of the object is acquired by means of an X-ray device.

10. A method as claimed in claim 1, wherein the three-dimensional image data set is acquired prior to introduction of the medical instrument into the object.

11. A method as claimed in claim 1, wherein the step of acquiring a two-dimensional X-ray image comprises the step of forming the X-ray image with a first beam path, further comprising the step of acquiring an additional two-dimensional X-ray image of the object using a second beam path perpendicular to the first beam path, the spatial correlation being determined between the acquired X-ray images and the acquired three-dimensional image data set.

12. A method as claimed in claim 1, wherein the step of determining the spatial position of the medical instrument comprises the steps of:

arranging light-emitting diodes in specific positions on the medical instrument; and providing a light-receiving element to receive the light emitted by the light-emitting diodes.

13. A method as claimed in claim 2, further comprising the step of selecting the at least one imaging element of the X-ray device from the group consisting of an X-ray source and an X-ray detector.

14. A method as claimed in claim 2, wherein the spatial positions of the at least one imaging element of the X-ray device are determined by means of a position measuring device.

15. A method as claimed in claim 2, wherein the step of determining the spatial position of the X-ray image comprises the steps of:

arranging light-emitting diodes in specific positions on the at least one imaging element; and providing a light-receiving element to receive the light emitted by the light-emitting diodes.

16. A method as claimed in claim 4, wherein the step of determining the spatial correlation by means of a comparison method further comprises the steps of determining a pseudo-projection image from at least a data sub-set of the three-dimensional image data set, comparing the pseudo-projection image with the X-ray image, and iteratively varying the parameters underlying the determination of the pseudo-projection image until optimum correspondence is achieved between the pseudo-projection image and the X-ray image.

17. A device for determining the position of a medical instrument, introduced into an object being examined, in a three-dimensional image data set of the object, the device comprising:

an X-ray device for acquiring a two-dimensional X-ray image of the object, a position measuring device for measuring the spatial positions of the X-ray image and the medical instrument when introduced into the object, and a processor arranged to determine the spatial correlation between the X-ray image and the three-dimensional image data set, and the position of the medical instrument in the three-dimensional image data set from the spatial position of the medical instrument using the spatial correlation between the X-ray image and the three-dimensional image data set.

18. A device as claimed in claim 17, wherein said X-ray device has a plurality of light-emitting diodes, said position measuring device including a light-receiving element for receiving light emitted by said diodes.

19. A device as claimed in claim 17, wherein said processor is arranged to generate an image from at least one of the three-dimensional image data set and the two-dimensional image acquired by said X-ray device and reproduced the position of the medical instrument in the generated image.

20. A method for determining the position of a medical instrument, partly introduced into an object being examined, in a three-dimensional image data set of the object, the method comprising the steps of:

acquiring a three-dimensional image data set of the object, acquiring a two-dimensional X-ray image of the object, determining spatial positions of the X-ray image and the medical instrument, determining a spatial correlation between the acquired X-ray image and the acquired three-dimensional image data set, and transforming the spatial position of the medical instrument into a position relative to the three-dimensional image data set using the determined spatial correlation between the acquired X-ray image and the acquired three-dimensional image data set to enable the reproduction of the position of the medical instrument in images derived from at least one of the three-dimensional image data set and the two-dimensional X-ray image.

* * * * *